United States Patent
Adachi

(10) Patent No.: US 8,639,010 B2
(45) Date of Patent: Jan. 28, 2014

(54) RADIOGRAPHIC APPARATUS

(75) Inventor: Susumu Adachi, Osaka (JP)

(73) Assignee: Shimadzu Corporation, Kyoto (JP)

(\*) Notice: Subject to any disclaimer, the term of this patent is extended or adjusted under 35 U.S.C. 154(b) by 102 days.

(21) Appl. No.: 13/502,455

(22) PCT Filed: Oct. 21, 2009

(86) PCT No.: PCT/JP2009/005521
§ 371 (c)(1),
(2), (4) Date: Apr. 17, 2012

(87) PCT Pub. No.: WO2011/048629
PCT Pub. Date: Apr. 28, 2011

(65) Prior Publication Data
US 2012/0219203 A1 Aug. 30, 2012

(51) Int. Cl.
*G06K 9/00* (2006.01)

(52) U.S. Cl.
USPC ............ 382/132; 382/128; 382/174; 382/175; 128/922; 128/923

(58) Field of Classification Search
USPC .................. 382/128, 130, 131, 132, 174, 175; 128/922, 923
See application file for complete search history.

(56) References Cited

U.S. PATENT DOCUMENTS

| | | | | |
|---|---|---|---|---|
| 5,530,735 A | * | 6/1996 | Gard et al. | 378/207 |
| 6,570,150 B2 | * | 5/2003 | Tsujii | 250/252.1 |
| 7,162,089 B2 | * | 1/2007 | Jin et al. | 382/199 |
| 7,486,406 B2 | * | 2/2009 | Kim | 356/497 |
| 7,689,055 B2 | * | 3/2010 | Zhang et al. | 382/254 |
| 2007/0040099 A1 | | 2/2007 | Yokoyama et al. | |

FOREIGN PATENT DOCUMENTS

| | | |
|---|---|---|
| JP | 7-72256 A | 3/1995 |
| JP | 2003-194949 A | 7/2003 |
| JP | 2006-305228 A | 11/2006 |
| JP | 2007-75598 A | 3/2007 |
| JP | 2009-189440 A | 8/2009 |

\* cited by examiner

*Primary Examiner* — Yosef Kassa

(74) *Attorney, Agent, or Firm* — McDermott Will & Emery LLP

(57) ABSTRACT

According to a radiographic apparatus of this invention, an image correcting unit corrects offset for every pixel relative to a detection value outputted from a radiation detector having pixels for detecting radiation arranged in a two-dimensional array. In addition, the image correcting unit corrects the offset while holding noise components contained in the detection value. Thus, upon quantitative evaluation of the noises contained in the detection values outputted from the radiation detector, the noises of not only positive values but also negative values can be considered. Consequently, accurate evaluation may be achieved.

6 Claims, 6 Drawing Sheets

RADIOGRAPHIC APPARATUS

CROSS REFERENCE TO RELATED APPLICATIONS

This application is a U.S. National Stage application under 35 U.S.C. §371 of International Application PCT/JP2009/005521 filed on Oct. 21, 2009, which was published as WO 2011/048629 A1 on Apr. 28, 2011. The application is incorporated herein by reference.

TECHNICAL FIELD

This invention relates to a radiographic apparatus for use in the medical field, and in the industrial field for performing a non-destructive testing and RI (Radio Isotope) inspection. More particularly, this invention is directed to a radiographic apparatus that enables accurate noise evaluation.

BACKGROUND

A flat-panel radiation detector is widely used as a radiation detector provided with a conventional radiographic apparatus. The flat-panel radiation detector has an active matrix substrate on which a radiation conversion layer is laminated. In particular, X-rays are to be taken an example of radiation. When an active matrix substrate is used for a flat-panel X-ray detector, detection pixels can be formed that detect X-rays for every active element. That is, an intensity of X-rays can be determined for every detection pixel.

When a semiconductor layer is used for an X-ray conversion layer, X-rays having entered into the X-ray conversion layer are converted into charge signals (carriers). The converted charge signals are accumulated in a capacitor for every detection pixel. The accumulated charge signals are read out for every detection pixel by an active matrix substrate. The read-out charge signals are converted into voltage signals while being amplified. An image processor forms an fluoroscopic image based on the voltage signals.

The voltage signals sent to the image processor as above contain electric circuit noises. Here, a voltage signal sent to the image processor is called an image signal. A value of the image signal corresponding to each detection pixel is called a pixel value. Data formed of pixel values for one frame is called image data. The image processor obtains noise signals in a dark image when the flat-panel X-ray detector is irradiated with no X-ray as offset components in order to remove the electric circuit noises. For instance, Japanese Patent Publication No. H07-72256A describes offset correction for removing offset components from the image signals obtained through imaging.

In recent years, moving images are often produced in connection with IVR (Interventional Radiology), etc. There arises a problem that a lag (residual image) due to a frame lag occurs upon producing moving images. Then, the need of accurately evaluating the lag increases.

Examples of guidelines for accurately evaluating the lag include evaluation by DQE (Detective Quantum efficiency). DQE is squared S/N ratio of input and output. For evaluation by the DQE, noises contained in the image data in the dark image need to be evaluated quantitatively.

This invention has been made regarding a state of the art noted above, and its object is to provide a radiographic apparatus that enables quantitative noise evaluation when no radiation is inputted.

SUMMARY

The inventor has made intensive research and thus attained the following findings. Specifically, in the conventional offset correction, no negative value is contained in the pixel value after offset correction regardless of X-ray emission. Upon performance of digital correction in which the offset components are subtracted from the obtained image data, a negative pixel value has been substituted to zero where the pixel value becomes a negative value less than zero by the offset correction, as shown in FIG. 7. Such offset correction presents no problem in the normal diagnostic imaging. That is because a range of negative pixel values is remarkably smaller than that of positive pixel values. The negative pixel values are substituted to zero, whereby image data can be easily processed and thus a load of image processing can be reduced.

On the other hand, when evaluation by DQE is performed, calculation is performed based on only a positive noise value. That is because a negative noise value is eliminated through the offset correction. This may lead to inaccurate evaluation by DQE. In other words, the offset correction interferes with accurate evaluation by DQE.

Examples of the invention are configured as described below to achieve the above object. The examples of this invention disclose a radiographic apparatus including an image correcting unit for correcting offset of a detection value for every pixel to output corrected image data, the detection value being outputted from a radiation detector having pixels for detecting radiation arranged in a two-dimensional array. The image correcting unit corrects the offset while holding noise components contained in the detection value.

According to an example the radiographic apparatus of this invention, the image correcting unit corrects the offset for every pixel relative to the detection value outputted from the radiation detector having pixels for detecting radiation arranged in a two-dimensional array. In addition, the image correcting unit corrects the offset while holding noise components contained in the detection value. Thus, upon quantitative evaluation of the noises contained in the detection value outputted from the radiation detector, the noises of not only positive values but also negative values can be considered. Consequently, accurate evaluation may be achieved.

Moreover, the image correcting unit may include an offset-parameter calculation unit, a fluctuation-noise calculation unit, a correction constant calculation unit, an offset correcting unit, and a gain correcting unit. The offset-parameter calculation unit calculates an offset parameter as a time average of the detection values for every pixel upon taking dark images. The fluctuation-noise calculation unit calculates a fluctuation noise that is a standard deviation of the detection values for every pixel upon taking the dark images. The correction constant calculation unit calculates a correction constant from the fluctuation noise for holding a negative value of a noise amplitude. The offset correcting unit calculates an offset correction value by subtracting the offset parameter from the detection value at which a subject is imaged and adding the correction constant. The gain correcting unit calculates corrected image data through multiplying a value, obtained by subtracting the correction constant from the offset correction value, by a gain correcting coefficient for correcting differences of the pixels in detecting property and then adding the correction constant.

With the above configuration, the offset-parameter calculation unit can calculate an offset parameter as a time average of detection values for every pixel upon taking dark images. Moreover, the fluctuation-noise calculation unit can calculate a fluctuation noise that is a standard deviation of the detection values for every pixel upon taking the dark images. The correction constant calculation unit can calculate a correction constant from the fluctuation noise for holding a negative value of a noise amplitude. The offset correcting unit can calculate an offset correction value by subtracting the offset parameter from the detection value at which a subject is imaged and adding the correction constant. The gain correcting unit can calculate corrected image data through subtracting the correction constant from the offset correction value, multiplying it by a gain correcting coefficient for correcting differences of the pixels in detecting property and then adding the correction constant. The correction constant is added to the noise of a negative value in the corrected image obtained in this way. Consequently, the noise of a negative value is raised up and the noise amplitude can be stored accurately in the corrected image data.

The correction constant calculation unit preferably calculates a correction constant based on a value of three times the fluctuation noise or more. Thereby, a noise amplitude contained in the detection value falls within the value of three times the standard deviation or more. Consequently, the noise value of a negative value can be raised up to a positive value. Moreover, the correction constant may be calculated based on $3\sigma$ that is three times the standard deviation. The correction constant may be the maximum of $3\sigma$ in every pixel.

Moreover, a display unit and an image constructing unit may be provided. The display unit displays a fluoroscopic image of the subject. The image constructing unit constructs the fluoroscopic image such that the corrected image data is set to correspond to a dynamic range of the display unit with the value of the correction constant as the minimum of a black level or the maximum of a white level. Consequently, the dynamic range of the display unit can be fully utilized, and the fluoroscopic image can have an enhanced contrast.

Moreover, the image correcting unit may include an offset-parameter calculation unit, an offset correcting unit, and a gain correcting unit. The offset-parameter calculation unit calculates an offset parameter as a time average of the detection values for every pixel upon taking dark images. The offset correcting unit calculates an offset correction value by subtracting the offset parameter from the detection value at which the subject is imaged. The gain correcting unit calculates corrected image data through multiplying the offset correction value by a gain correcting coefficient for correcting differences of the pixels in detecting property. The offset correcting unit and the gain correcting unit may perform calculation with plus and minus signs. The corrected image data to which gain correction has been performed in the gain correcting unit is image data with plus and minus signs. Such configuration may be adopted. With this configuration, the corrected image is image data with plus and minus signs. Consequently, the noise signals of negative values upon taking the dark image can be stored accurately in the corrected image.

According to the radiographic apparatus of this invention, a radiographic apparatus can be provided that enables quantitative noise evaluation when no radiation is inputted.

DETAILED DESCRIPTION

Figure 1:
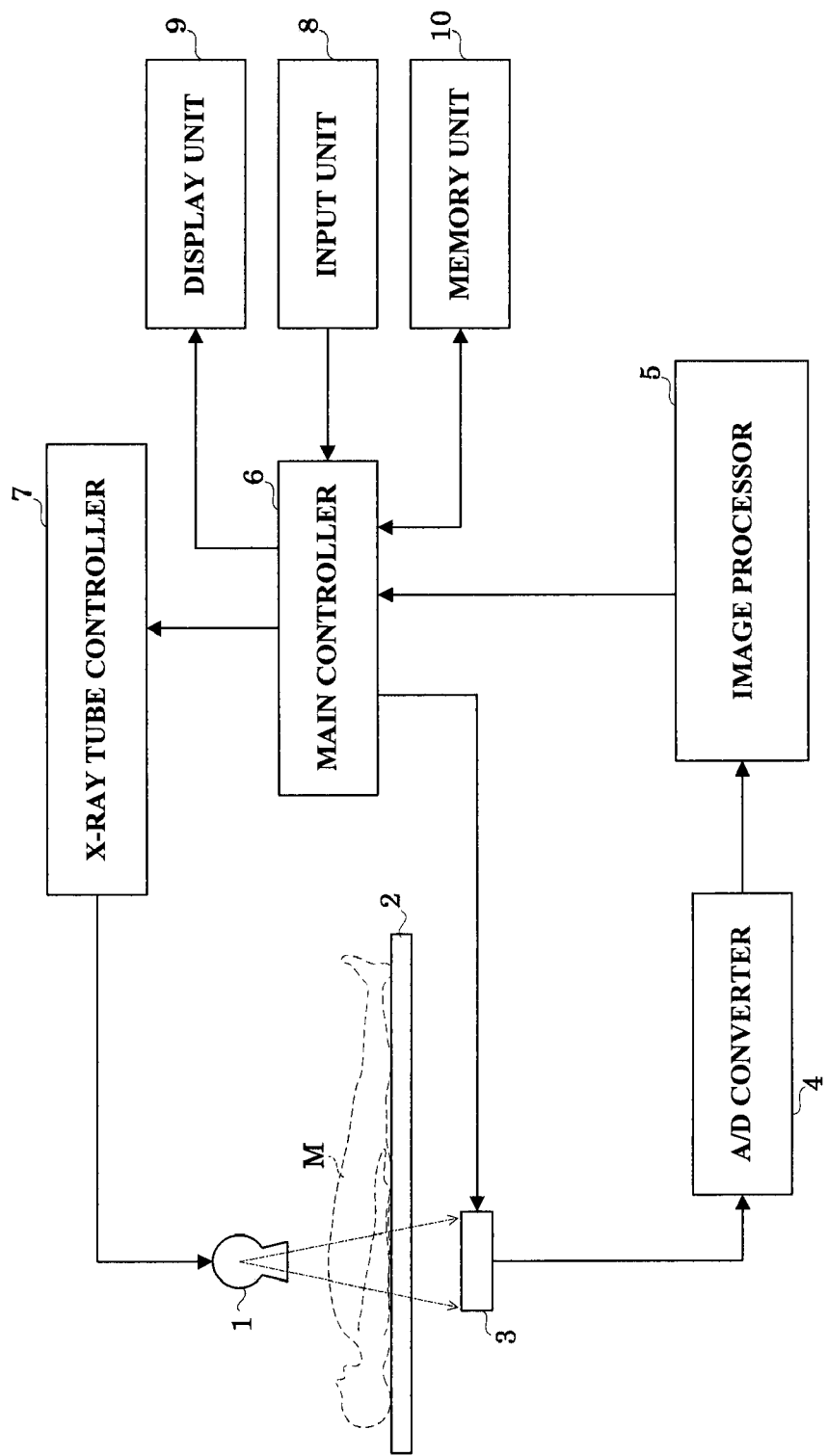
FIG. 1 is a block diagram showing an overall construction of an X-ray apparatus according to an example.
Figure 2:
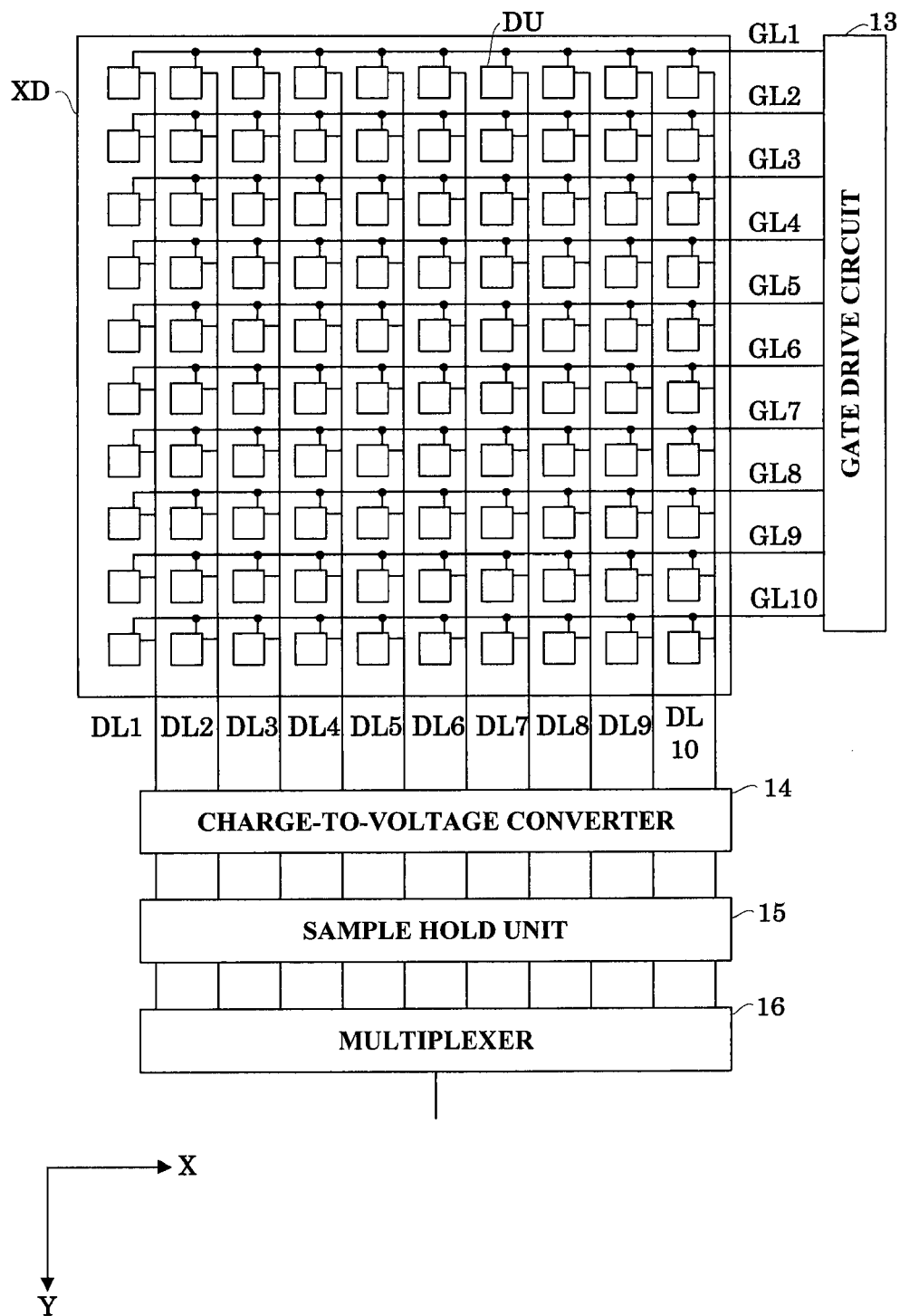
FIG. 2 is a block diagram showing a construction of a flat X-ray detector according to the example.
Figure 3:
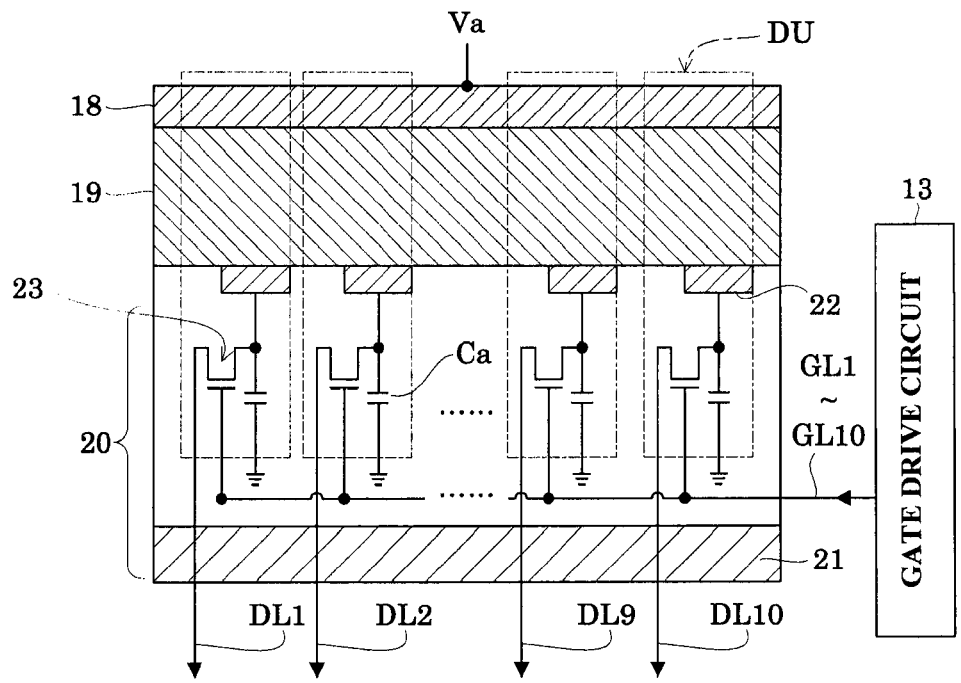
FIG. 3 is a schematic sectional view around an X-ray conversion layer Of the flat X-ray detector according to the example.

An example of the invention is described in detail hereinafter with reference to the drawings. FIG. 1 is a block diagram showing an overall construction of an X-ray apparatus according to this example. FIG. 2 is a block diagram showing a construction of a flat-panel X-ray detector provided with the X-ray apparatus. FIG. 3 is a schematic sectional view around an X-ray conversion layer of the flat-panel X-ray detector according to the example. The example is described, taking X-rays as an example of incident radiation, and an X-ray apparatus as an example of the radiographic apparatus.

X-Ray Apparatus

As shown in FIG. 1, the X-ray apparatus includes an X-ray tube 1 for irradiating a subject M as an object to be imaged with X-rays, a top board 2 for supporting the subject M, a flat-panel X-ray detector (hereinafter, referred to as an FPD) 3 for detecting X-rays by converting X-rays into charge signals in accordance with an amount of X-rays transmitted through the subject M and then converting the charge signals into voltage signals to output them, and an analog-to-digital converter 4 for converting the voltage signals from the FPD 3 from analog signals to digital signals.

The X-ray apparatus further includes an image processor 5 for processing the digital voltage signals converted in the A/D converter 4 to construct a fluoroscopic image, a main controller 6 for performing various control with respect to X-ray imaging, an X-ray tube controller 7 for controlling a tube voltage and a tube current to be generated in the X-ray tube 1 in accordance with the control by the main controller 6, an input unit 8 for inputting various settings with respect to the X-ray imaging, a display unit 9 for displaying the fluoroscopic image obtained by the image processor 5, and a storage unit for storing the fluoroscopic image obtained by the image processor 5.

The input unit 8 is formed of a keyboard, a mouse, and a joystick. The display unit 9 is formed of a CRT or a liquid crystal monitor. The storage unit 10 is formed of a ROM or RAM. The image processor 5, the main controller 6, and the X-ray tube controller 7 include a central processing unit (CPU). The image processor 5, the main controller 6, and the storage unit 10 may be formed in a host computer. Description is given next in detail of each element in the X-ray apparatus.

As shown in FIG. 2, the FPD 3 includes a plurality of detection pixels DU(x, y), a gate drive circuit 13, a charge-to-voltage converter 14, a sample hold unit 15, and a multiplexer 16. The plurality of detection pixels DU(x, y) are connected to the gate drive circuit 13 via gate lines GL1 to GL10 and to the charge-to-voltage converter 14 via data lines DL1 to DL10. The detection pixels DU(x, y) correspond to pixels in this invention. The FPD 3 corresponds to the radiation detector in this invention.

The detecting pixels DU are operable in response to incident X-rays, and output charge signals. The detecting pixels DU are arranged in rows and columns in a two-dimensional matrix form on an X-ray detector XD into which X-rays enter. Here, an index (x, y) represents a position of each detection pixel DU. Moreover, FIG. 2 shows the detection pixels DU(x, y) arranged in a two-dimensional matrix form in ten rows in a vertical (Y) direction by ten columns in a horizontal (X) direction as one example. Actually, approximately 4096 by 4096 detection pixels DU(x, y) are arranged in rows and columns in a two-dimensional matrix form on the X-ray detector XD.

As shown in FIG. 3, the detection pixels DU(x, y) includes a voltage application electrode 18 to which a high bias voltage Va is applied, an X-ray conversion layer 19 for converting incident X-rays into charge signals, and an active matrix substrate 20 for reading out (outputting) the charge signals converted by the X-ray conversion layer 19.

The X-ray conversion layer 19 consists of an X-ray sensitive semiconductor, and is formed of such as CdTe (cadmium telluride) or CdZnTe (zinc telluride cadmium) that is a polycrystalline compound semiconductor, or α-Se (amorphous selenium). When X-rays enter into the X-ray conversion layer 19, a given number of charge signals (carriers) proportional to the energy of these X-rays are directly generated. Thus, the FPD 3 is a direct-conversion type flat-panel X-ray detector. Moreover, an electric field occurs in the X-ray conversion layer 19 due to the bias voltage Va applied to the voltage application electrode 18. Thus, the generated charge signals are collected for every pixel electrode 22.

The active matrix substrate 20 as in FIG. 3 includes a glass substrate 21 having electrical insulation properties. On the glass substrate 21, the active matrix substrate 20 includes a capacitor Ca for accumulating the charge signals collected for every pixel electrode 22, a thin film transistor (hereinafter, referred to as a TFT) 23 as a switching element, gate lines GL1 to GL10 for controlling the TFT 23 from the gate drive circuit 13, and data lines DL1 to DL10 through which the charge signals are read out from the TFT 23.

The gate drive circuit 13 operates the TFT 23 of each detection pixel DU(x, y) for selecting and fetching the charge signals detected by the detection pixel DU(x, y) sequentially. The gate drive circuit 13 sequentially selects the gate lines GL1 to GL10 connected in common to every row of the detection pixels DU(x, y), and sends gate signals. The TFTs 23 of the detection pixel DU(x, y) in the selected row are switched on simultaneously by the gate signals. The charge signals accumulated in the capacitor Ca are outputted to the charge-to-voltage converter 14 via the data lines DL1 to DL10.

Figure 4:
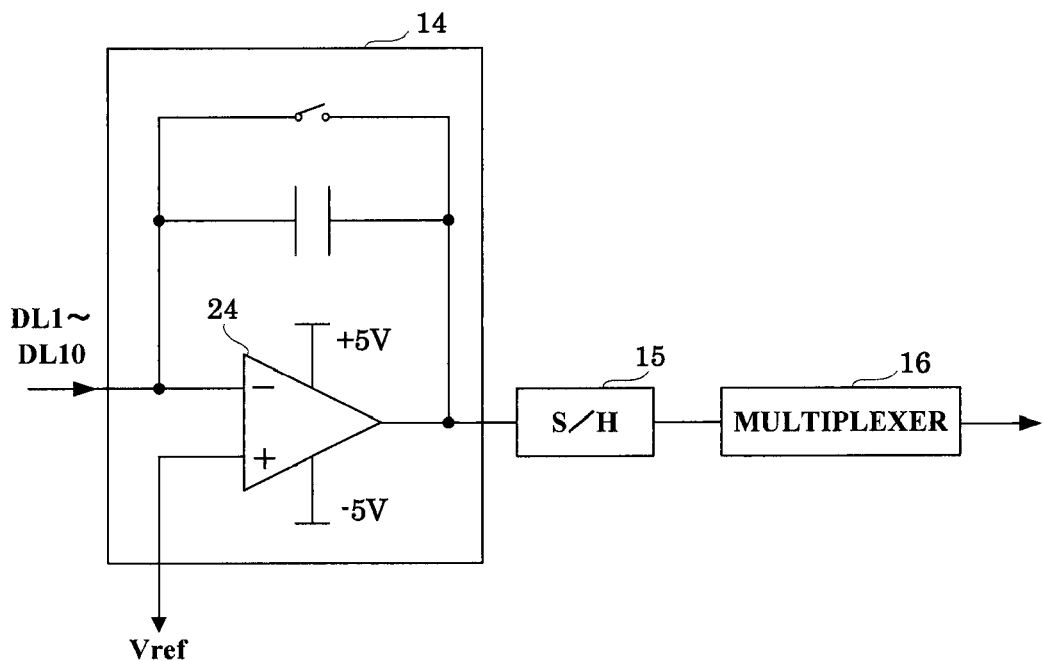
FIG. 4 is a circuit diagram showing a construction of a charge-to-voltage converter according to the example.

Next, the charge-to-voltage converter 14 as in FIG. 4 includes a number of charge-to-voltage converting amplifiers 24, the number corresponding to the data lines DL1 to DL10 (FIG. 2 ten pieces) provided for every column of the detection pixel DU(x, y). The charge-to-voltage converting amplifier 24 is a charge sensitive amplifier (CSA) circuit for converting the charge signals outputted from each detection pixel DU(x, y) into voltage signals. The charge-to-voltage converting amplifier 24 converts the charge signals read from the data lines DL1 to DL10 into voltage signals.

Power supply voltages of +5V and −5V are applied to the charge-to-voltage converting amplifier 24. Where input signals to the charge-to-voltage converting amplifier 24 are of negative values, the charge-to-voltage converting amplifier 24 conventionally outputs signals of a zero value. That is, an output width of the conventional charge-to-voltage converting amplifier is from 0V to +5V. In the example, however, where input signals to the charge-to-voltage converting amplifier 24 is of negative values, voltage signals of negative values are outputted. That is, the charge-to-voltage converting amplifier 24 outputs signals from −5V to +5V. Thus, the charge-to-voltage converting amplifier 24 outputs voltage signals with plus and minus signs to the sample hold unit 15.

Next, the sample hold unit 15 includes a number of sample hold circuits, the number corresponding to the number of the charge-to-voltage converting amplifier 24 of the charge-to-voltage conversion unit 14. The voltage signals outputted from the charge-to-voltage converting amplifier 24 are sampled for a given time in advance. The voltage signals are held after the given time elapses. The voltage signals in a stable state are outputted to the multiplexer 16. The sample hold unit 15 can process voltage signals with both positive and negative values.

Next, the multiplexer 16 includes inside thereof a number of switches, the number corresponding to the number of sample hold circuits. The multiplexer 16 switches one of the switches to an ON state sequentially, and outputs each voltage signal outputted from each sample hold circuit as a bundled time-division signal to the A/D converter 4. The A/D converter 4 samples the voltage signals from the multiplexer 16 at a given timing, converts them into digital voltage signals, and outputs them to the image processor 5. The multiplexer 16 and the A/D converter 4 can process voltage signals with both positive and negative values.

Image Processor

Description is given of image data composed of voltage signals inputted into the image processor 5. Dark image data DI(x, y, t) acquired upon obtaining a dark image with no radiation emitted is formed of an offset parameter Io(x, y) containing no time fluctuation noise and a time fluctuation noise In(x, y, t). That is, dark image data DI(x, y, t) can be expressed as follows.

$$DI(x,y,t)=Io(x,y)+In(x,y,t) \quad (1)$$

The offset parameter Io(x, y) containing no time fluctuation noise can be determined through obtaining a few tens of dark images and calculating a time average of the dark image data DI(x, y, t) for every detection pixel DU(x, y). In other words, among noises contained in the image data, the offset parameter Io(x, y) is a noise component that has no time fluctuation.

$$Io(x,y)=Ave[DI(x,y,t)] \quad (2)$$

That is, the time fluctuation noise In(x, y, t) is a noise signal having a calculated time average of zero.

$$Ave[In(x,y,t)]=0 \quad (3)$$

The time fluctuation noises In(x, y, t) as electric circuit noises cause the voltage signals inputted into the image processor 5 to have negative values. Then the voltage signals to be inputted are raised up by a fluctuation range of the time fluctuation noises In(x, y, t), whereby the image data after offset correction can have a positive value. Specifically, the temporal fluctuation range of the time fluctuation noise In(x, y, t) for each detection pixel DU(x, y) is calculated as a standard deviation σ, and then 3σ is calculated as three times the value of the standard deviation σ.

Here, let the temporal standard deviation a of the time fluctuation noise In(x, y, t) be a fluctuation noise Ns(x, y), and a value of 3σ be a fluctuation value FA(x, y). The fluctuation noise Ns(x, y) is determined through calculating a standard deviation to every detection pixel DU(x, y) of data on a few tens of obtained dark images DI(x, y, t). In addition, let the maximum in all pixels of fluctuation values FA(x, y) calculated from the fluctuation noises Ns(x, y) for every detection pixel DU(x, y) be a fixed value M. The fixed value M is added to the pixel value in offset correction and gain correction, whereby the corrected image data can be of positive values while the noises upon no input with no incident radiation remain accurately in the corrected image data.

$$Ns(x, y) = \sigma \quad (4)$$
$$= Stdev[In(x, y, t)]$$
$$= Stdev[DI(x, y, t)] \quad (5)$$
$$FA(x, y) = 3 \cdot \sigma \quad (6)$$
$$= 3 \cdot Ns(x, y)$$

Description will be given next of the picked-up image data I(x, y, t) with X-rays transmitted through the subject. The picked-up image data I(x, y, t) is formed of image components Ia(x, y, t) and offset components Ib(x, y, t) containing time fluctuation noises. Consequently, the picked-up image data I(x, y, t) can be expressed as follows.

$$I(x,y,t)=Ia(x,y,t)+Ib(x,y,t) \quad (7)$$

The offset component Ib(x, y, t) contains the time fluctuation noise having noise components varying with time. Thus the value of the offset component Ib(x, y, t) varies for every imaging. The offset component Ib(x, y, t) can be expressed as follows with the offset parameter Io(x, y) and the time fluctuation noise In(x, y, t):

$$Ib(x,y,t)=Io(x,y)+In(x,y,t) \quad (8)$$

In other words, by Equations (1) and (8), the offset component Ib(x, y, t) is expressed as a noise component upon imaging of the subject M with no incident radiation.

Figure 5:
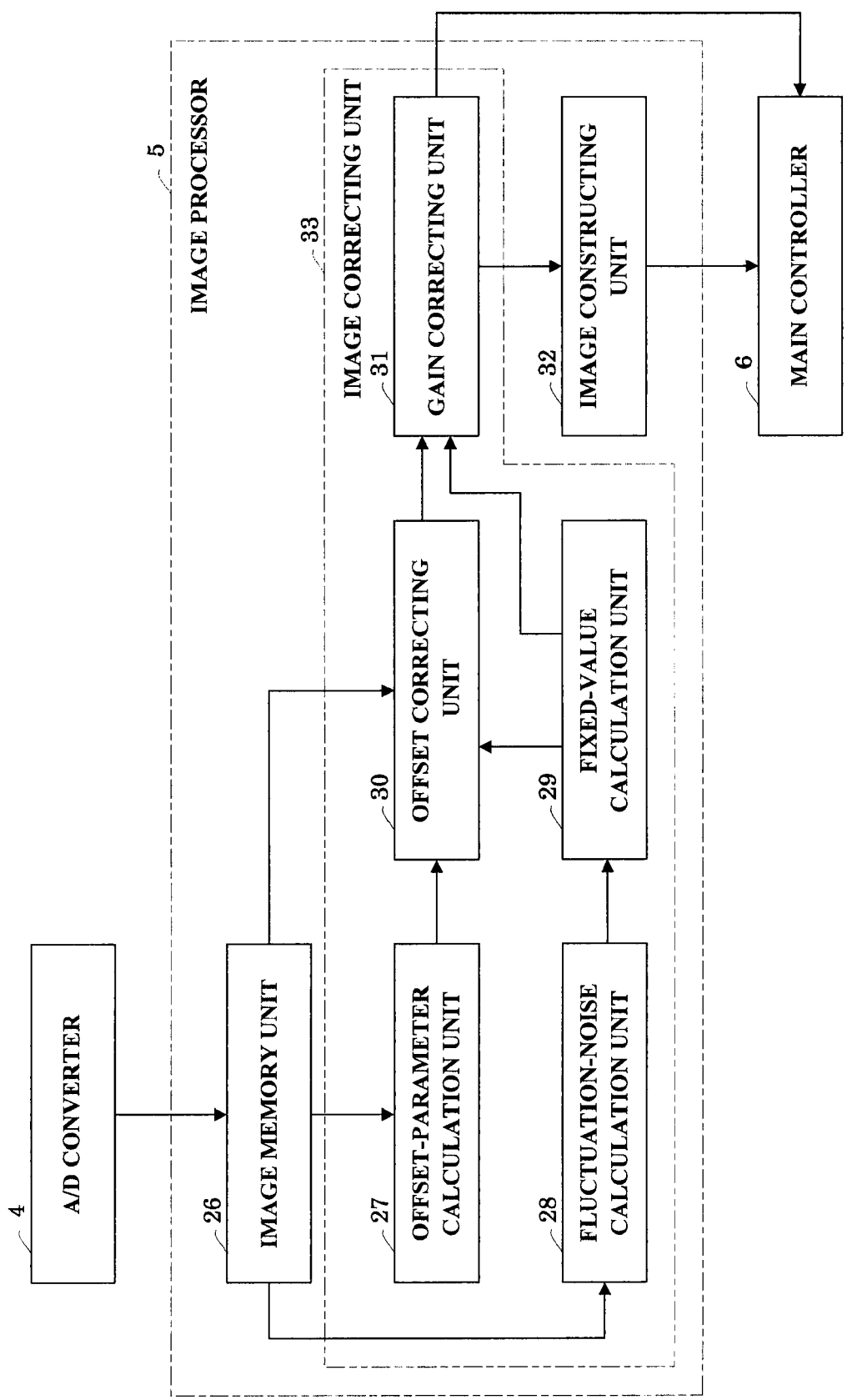
FIG. 5 is a block diagram showing a construction of an image processor according to the example.

Next, the construction of the image processor 5 is described. The image processor 5 as in FIG. 5 includes an image memory unit 26 for storing image data, an image correcting unit 33 for performing offset correction and gain correction to the image data stored in the image memory unit 26, and an image constructing unit 32 for constructing a fluoroscopic image from the picked-up image data to which the gain correction has been performed. The image correcting unit 33 includes an offset-parameter calculation unit 27 for calculating an offset parameter, a fluctuation-noise calculation unit 28 for calculating a fluctuation noise Ns(x, y), a fixed-value calculation unit 29 for calculating a fixed value M that raises up the image data, an offset correcting unit 30 for removing the offset parameter from the picked-up image data, and a gain correcting unit 31 for correcting differences of each detection pixel DU(x, y) in detecting property. The image processor 5 performs offset correction and gain correction to the pixel values transferred from the FPD 3 to the A/D converter 4 to construct a fluoroscopic image.

The digital voltage signals outputted from the A/D converter 4 are stored in the image memory unit 26 as pixel values that are image data for every detection pixel DU(x, y). The image memory unit 26 also functions as a buffer of image data.

The offset-parameter calculation unit 27 calculates the offset parameter Io(x, y) in advance upon dark image acquisition. Specifically, the offset-parameter calculation unit 27 calculates an average value of the dark image data DI(x, y, t) for every detection pixel DU(x, y) as in Equation (2) based on the dark image data DI(x, y, t) stored in the image memory unit 26 through obtaining a few tens of dark images, thereby calculating the offset parameter Io(x, y) with no time fluctuation noise. The calculated offset parameter Io(x, y) is transferred to the offset correcting unit 30.

The fluctuation-noise calculation unit 28 calculates the standard deviation a of the data on a few tens of dark images DI(x, y, t) stored in the image memory unit 26 as in Equation (5), thereby calculating the fluctuation noise Ns(x, y) for every detection pixel DU(x, y) in the dark images. The fluctuation noise Ns(x, y) calculated for every detection pixel DU(x, y) in the dark images is transferred to the fixed-value calculation unit 29.

The fixed-value calculation unit 29 calculates a fluctuation value FA(x, y), three times the fluctuation noise Ns(x, y), as in Equation (6). In addition, the fixed-value calculation unit 29 calculates the maximum in all detection pixels DU(x, y) of the fluctuation values FA(x, y) calculated for every detection pixel DU(x, y). Let the maximum be a fixed value M. The calculated fixed value M is transferred to the offset correcting unit 30. The fixed value M corresponds to the correction constant in this invention. The fixed-value calculation unit 29 corresponds to the correction-constant calculation unit in this invention.

The offset correcting unit 30 calculates difference between the image data I(x, y, t) transferred from the image memory unit 26 and the offset parameter Io(x, y) calculated by the offset-parameter calculation unit 27, and adds the fixed value M, thereby calculating an offset correction value $J_1$(x, y, t). Consequently, the offset parameter Io(x, y) that is a noise component with no time fluctuation can be removed from the image data I(x, y, t).

$$J_1(x, y, t) = M + I(x, y, t) - Io(x, y) \quad (9)$$
$$= M + Ia(x, y, t) + \{Ib(x, y, t) - Io(x, y)\}$$
$$= Ia(x, y, t) + M + In(x, y, t)$$

The first term of Equation (9) corresponds to an image component, the second term corresponds to a raised component for holding a fluctuation range of the time fluctuation noise, and the third term corresponds to the time fluctuation noise. For instance, the offset correction value $J_1$(x, y, t) in the pixel in which the image component and the time fluctuation noise are zero has the fixed value M. That is, a zero point of the image data is raised up to the fixed value M compared to that before offset correction. Consequently, with the image component of a zero value and the time fluctuation noise of a negative value, the offset correction value $J_1$(x, y, t) is raised up with the fixed value M. Thus, the offset correction value $J_1$(x, y, t) can have a positive value, and the time fluctuation noise upon taking the dark image can remain accurately.

The gain correcting section 31 stores a gain correcting coefficient $I_G$(x, y) determined in advance in order to make X-ray conversion efficiencies uniform for every detection pixel DU(x, y). The gain correcting section 31 multiplies the difference between the offset correction value $J_1$(x, y, t) and the fixed value M by the gain correcting coefficient $I_G$(x, y) and adds to it the fixed value M, thereby achieving calculation of corrected image data $K_1$(x, y, t) after gain correction.

$$K_1(x, y, t) = \{J_1(x, y, t) - M\} \cdot I_G(x, y) + M \quad (10)$$
$$= Ia(x, y, t) \cdot I_G(x, y) + M + In(x, y, t) \cdot I_G(x, y)$$

The first term of Equation (10) corresponds to image data after gain correction. The second term corresponds to a component raised by the fluctuation range of the time fluctuation noise. The third term corresponds to the time fluctuation noise component after gain correction. Here, the gain correcting coefficient $I_G$(x, y) is close to 1. Thus, the component value of the time fluctuation noise after gain correction does not exceed the fixed value M.

Consequently, when image data of one detection pixel DU(x, y) after gain correction is of a zero value and the time fluctuation noise In(x, y, t) is of a negative value, the corrected image data $K_1$(x, y, t) is not less than a zero value, since the fixed value M is added. As noted above, the noises of the image data corresponding to those taken with no radiation emission are also stored accurately also in the corrected image data $K_1$(x, y, t) after gain correction.

The image constructing unit 32 constructs a fluoroscopic image based on the corrected image data $K_1$(x, y, t) to which the gain correcting unit 31 performs gain correction. At this time, image data is mapped with the fixed value M as the minimum of a black level or the maximum of a white level. That is, on the fluoroscopic image, a pixel value lower than the fixed value M is substituted to a tone value of the minimum of the black level or the maximum of the white level. Moreover, the image constructing unit 32 can reconstruct not only a fluoroscopic image, but also a tomogram upon CT imaging. The constructed fluoroscopic image is transferred to the main controller 6, and then is displayed on the display unit 9 or is stored in the storage unit 10. The corrected image data $K_1$(x, y, t) after gain correction is also transferred to the main controller 6, and is stored in the storage unit 10. DQE can be correctly evaluated in accordance with the corrected image data $K_1$(x, y, t) stored in the storage unit 10.

X-Ray Imaging

Description is given next of operation of X-ray imaging with the X-ray apparatus in the example with reference to FIGS. 1 to 5.

First, in response to instructions from the input unit 8 to start X-ray imaging, the main controller 6 controls the X-ray tube controller 7 and the FPD 3. The X-ray tube controller 7 controls the X-ray tube 1 to generate tube currents and tube voltages. The X-ray tube 1 irradiates the subject M with X-rays. X-rays transmitted through the subject M are converted by the detection pixels DU(x, y) of the FPD 3 into charge signals having an amount corresponding to that of X-rays transmitted through the subject M. The charge signals are accumulated in the capacitor Ca.

Next, the gate drive circuit 13 selects a gate line sequentially. The example describes selection of each gate line GL1, GL2, GL3, . . . , GL9 and GL10 in this order. The gate drive circuit 13 selects the gate line GL1 to specify each detection pixel DU(x, y) connected to the gate line GL1. Gate signals are sent to the gate of the TFT 23 in each specified detection pixel DU(x, y), whereby voltages are applied to turn the gate ON. Consequently, the charge signals accumulated in the capacitor Ca connected to each specified TFT 23 are read out to the data lines D1 to D10 via the TFT 23. Next, the drive circuit 13 selects the gate line GL2 to specify each detection pixel DU(x, y) connected to the gate line GL2 in the same process. The charge signals accumulated in the capacitor Ca of each specified detection pixel DU(x, y) are read out to the data lines D1 to D10. The other gate lines GL3 to GL10 are similarly selected in turn, whereby charge signals are read out two-dimensionally.

As noted above, the gate drive circuit 13 selects the gate lines GL1 to GL10 sequentially. Thereby, each detection pixel DU(x, y) connected to each gate line is specified, and the charge signals accumulated in the capacitor Ca of each specified detection pixel DU(x, y) are read out to the data lines D1 to D10.

The charge-to-voltage conversion unit 14 converts the charge signals that are read out to each data lines DL1 to DL10 into voltage signals, and amplifies them. Next, the sample hold unit 15 samples the voltage signals converted in the charge-to-voltage conversion unit 14, and temporarily holds them. Subsequently, the multiplexer 16 sequentially outputs the voltage signals held by the sample hold unit 15 as time dividing signals. The A/D converter 4 converts the outputted voltage signals from analog to digital values. The voltage signals converted into digital values are sent to the image processor 5.

The picked-up image data I(x, y, t) composed of the voltage signals sent to the image processor 5 are stored in the image memory unit 26. The data on a plurality of dark images DI(x, y, t) having collected image data with no X-ray emitted in advance is also stored in the image memory unit 26. The offset-parameter calculation unit 27 averages the data on a few tens of dark images DI(x, y, t) for every detection pixel DU(x, y) to calculate an offset parameter Io(x, y). The fluctuation-noise calculation unit 28 determines the fluctuation noise Ns(x, y) through calculating a standard deviation a to every detection pixel DU(x, y) from the data on a plurality of dark images DI(x, y, t).

The fixed-value calculation unit 29 calculates a fluctuation value FA(x, y) as a value three times the fluctuation noise Ns(x, y). In addition, the fixed-value calculation unit 29 calculates a fixed value M, the fixed value M being the maximum in all detection pixels DU(x, y) of the fluctuation values FA(x, y) calculated for every detection pixel DU(x, y).

Subsequently, the offset correcting unit 30 calculates the offset correction value $J_1$(x, y, t) from the picked-up image data I(x, y, t) stored in the image memory unit 26, the offset parameter Io(x, y) calculated by the offset-parameter calculation unit 27, and the fixed value M calculated by the fixed-value calculation unit 29. Thereby, a zero point of the image data is raised up to the fixed value M. Moreover, the offset parameter Io(x, y) that is a noise component with no time fluctuation is removed from the image data I(x, y, t), whereby the offset correction value $J_1$(x, y, t) can be obtained.

Moreover, detection efficiency that differs in every detection pixel DU(x, y) can be corrected by performing gain correction to the offset correction value $J_1$(x, y, t). Specifically, the fixed value M is temporarily subtracted from the offset correction value $J_1$(x, y, t), the result is multiplied by the gain correcting coefficient, and then the fixed value M is added to it. Thus, gain correction can be performed. Thus, the noises corresponding to the time fluctuation noises In(x, y, t) upon taking the dark image also remain accurately in the corrected image data $K_1$(x, y, t) after gain correction. Consequently, DQE of the imaging apparatus can be evaluated from the corrected image data $K_1$(x, y, t).

The image constructing unit 32 constructs a fluoroscopic image based on the corrected image data $K_1$(x, y, t) calculated as above. At this time, image data is mapped with the fixed value M as the minimum of a black level or as the maximum of a white level. That is, the corrected image data $K_1$(x, y, t) is set as to correspond to the dynamic range of the display unit 9. On the fluoroscopic image, a pixel value lower than the fixed value M is substituted to a tone value of the minimum of the black level or the maximum of the white level. The constructed fluoroscopic image is transferred to the main controller 6, and then is displayed on the display unit 9 or is stored in the storage unit 10. The corrected image data $K_1$ (x, y, t) is also stored in the storage unit 10 through the main controller 6.

According to the example above, the image correcting unit 33 can hold the time fluctuation noise In(x, y, t) contained in the picked-up image data I(x, y, t), and can perform offset correction. Moreover, when the picked-up image has the pixel value of zero, plus/minus noise amplitudes are accurately contained in the corrected image data after gain correction. Thus, an amount of noises with no X-ray emission can be evaluated quantitatively. Consequently, DQE prescribed by international standards can be accurately calculated.

When calculation including negative values is performed, the positive maximum of the tone value of the image data has to be reduced by half of the conventional value, or the bit number of the image has to be increased. Addition of the fixed value M, however, can maintain the tone with the same image bit number as the conventional one. That is because the fluctuation noises containing negative data are raised up to have positive values. Consequently, every corrected image data has a positive value not less than zero, and thus every image data can have a range of a positive value. As a result, a high dynamic range can be maintained.

In the foregoing example, addition of the fixed value M causes the corrected image data $K_1(x, y, t)$ after gain correction to have a positive value. Then, when the bit number of the corrected image data after gain correction is increased and a bit only for signs is provided, negative values can remain in the corrected image data after gain correction. Consequently, the fixed value M does not need to be calculated. Herein, the negative values of the corrected image data are used only for calculation of DQE.

Figure 6:
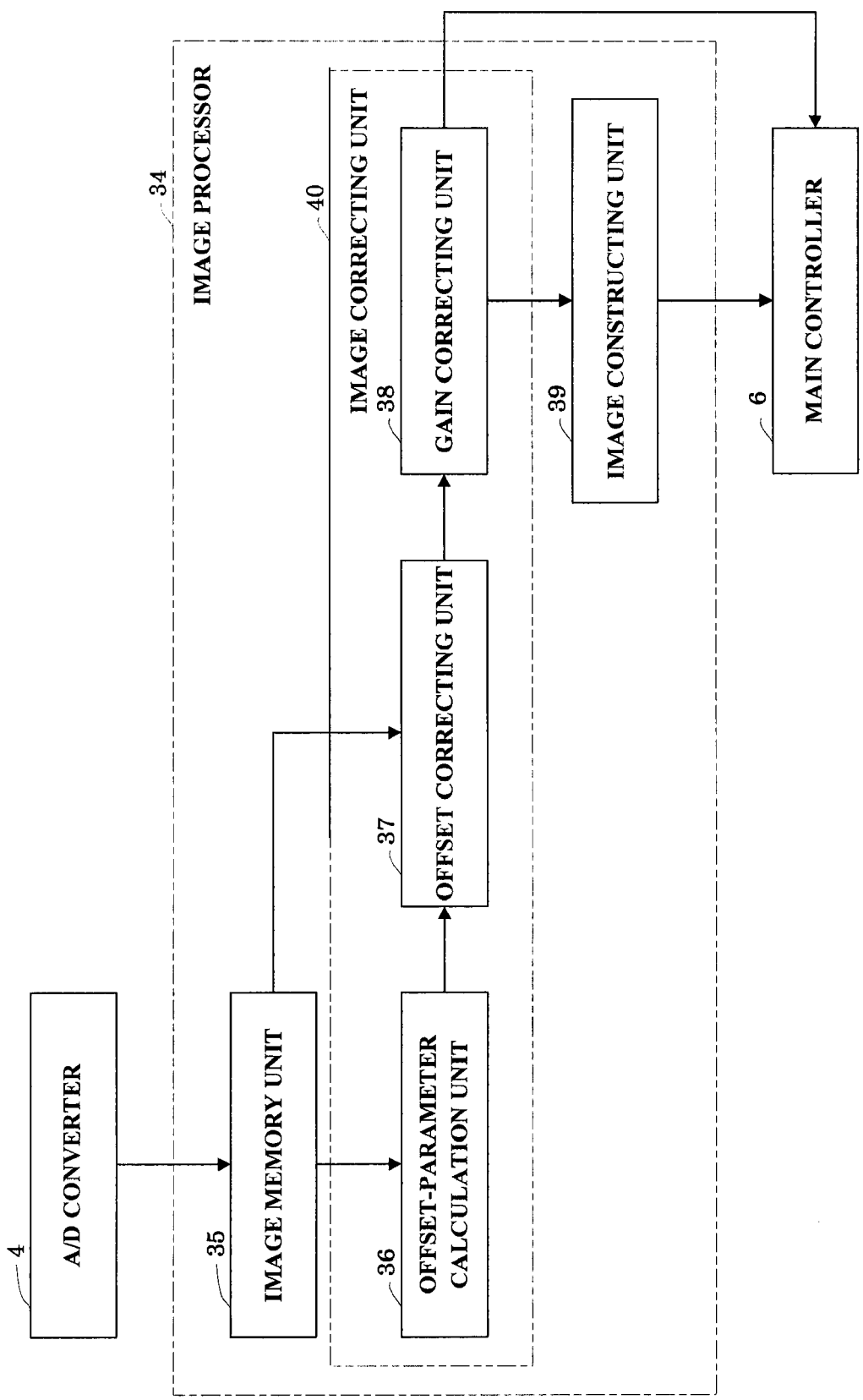
FIG. 6 is a block diagram showing a construction of an image processor according to another example.
Figure 7:
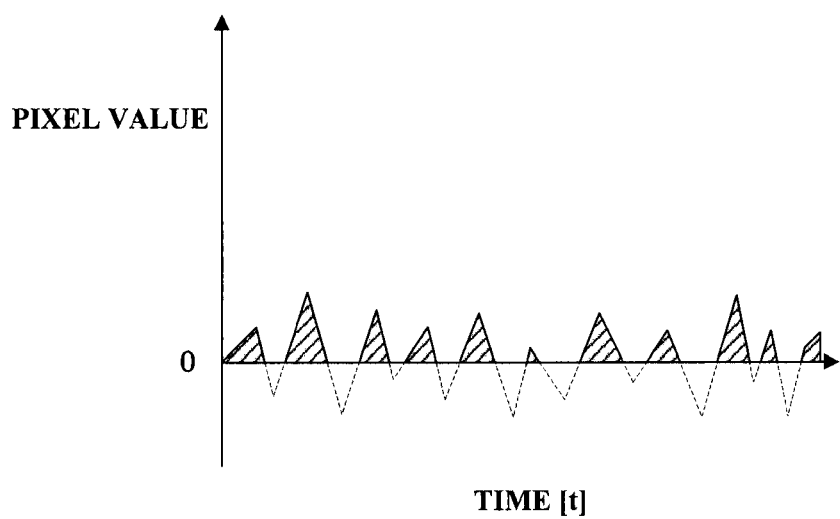
FIG. 7 an explanatory view of image output after offset correction according to the conventional embodiment.

An image processor 34 in this embodiment as in FIG. 6 is formed of an image memory unit 35, an image correcting unit 40, and an image constructing unit 39. The image correcting unit 40 is formed of the offset-parameter calculation unit 36, an offset correcting unit 37, and a gain correcting unit 38. This example differs from above example in that corrected image data $K_2(x,y,t)$ after gain correction may have a negative value since the data is not raised up with the fixed value M. Thus, this example has no feature corresponding to the correction constant calculation unit 28. Description is given hereinafter only of the difference between examples, and description of common aspects are to be omitted.

An offset-parameter calculation unit 36 calculates the offset parameter Io(x, y) in advance upon dark image acquisition. Specifically, the offset-parameter calculation unit 36 calculates an average value of the dark image data DI(x, y, t) for every detection pixel DU(x, y) as in Equation (2) based on the dark image data DI(x, y, t) stored in the image memory unit 35 through obtaining a few tens of dark images, thereby calculating an offset parameter Io(x, y) with no time fluctuation noise In(x, y, t). The calculated offset parameter Io(x, y) is transferred to the offset correcting unit 37.

The offset correcting unit 37 calculates difference between the image data I(x, y, t) transferred from the image memory unit 35 and the offset parameter Io(x, y) calculated by the offset-parameter calculation unit 36, thereby calculating an offset correction value $J_2(x, y, t)$. Consequently, the offset parameter $I_0(x, y)$ that is a noise component with no time fluctuation can be removed from the image data I(x, y, t). At this time, the offset correction value $J_2(x, y, t)$ is a value with plus and minus signs.

$$J2(x, y, t) = I(x, y, t) - Io(x, y) \quad (11)$$
$$= Ia(x, y, t) + \{Ib(x, y, t) - Io(x, y)\}$$
$$= Ia(x, y, t) + In(x, y, t)$$

The first term of Equation (11) corresponds to an image component, and the second term corresponds to the time fluctuation noise component. The second term may include a negative value. The image data is data with plus and minus signs in the present example. Consequently, when the image component is zero and the time fluctuation noise is a negative value, the time fluctuation noise can remain in the offset correction value $J_2$ (x, y, t) accurately upon taking the dark image.

The gain correcting section 38 stores a gain correcting coefficient $I_G(x, y)$ determined in advance in order to make X-ray conversion efficiencies uniform for every detection pixel DU(x, y). The gain correcting section 38 multiplies the offset correction value $J_2$ (x, y, t) by the gain correcting coefficient $I_G(x, y)$, thereby achieving calculation of corrected image data $K_2$ (x, y, t) after gain correction.

$$K_2(x, y, t) = J_2(x, y, t) \cdot I_G(x, y) \quad (12)$$
$$= Ia(x, y, t) \cdot I_G(x, y) + In(x, y, t) \cdot I_G(x, y)$$

The first term of Equation (12) corresponds to image data after gain correction. The second term corresponds to the time fluctuation noise component after gain correction. Thus, the time fluctuation noise In(x, y, t) of a negative value and the pixel value of not less than zero may be stored in the pixel in which the picked-up image data after gain correction is zero. As noted above, the fluctuation noise with offset upon no input is stored accurately also in the corrected image data $K_2$ (x, y, t) after gain correction.

The image constructing unit 39 constructs a fluoroscopic image based on the corrected image data $K_2$ (x, y, t) to which the gain correcting unit 38 performs gain correction. At this time, each image data is mapped with a zero value as the minimum of a black level or as the maximum of a white level. That is, on the fluoroscopic image, a pixel value lower than zero is substituted to a tone value of the minimum of the black level or the maximum of the white level.

As noted above, in this example, when the picked-up image has the pixel value of zero, plus/minus noise amplitudes due to the fluctuation noises are accurately contained in the corrected image data after correction. Thus, an amount of noises with no X-ray emission can be evaluated quantitatively. Consequently, DQE prescribed by international standards can be accurately calculated.

This invention is not limited to the foregoing examples, but may be modified as follows.

(1) In the foregoing examples, let a value 3σ that is three times a standard deviation σ be a fluctuation value FA(x, y). Alternatively, a fluctuation value FA(x, y) may be a value that is three times a standard deviation or more.

(2) In the foregoing examples, the image constructing unit 32 maps each image data with the fixed value M as the minimum of a black level or as the maximum of a white level. Alternatively, each image data may be mapped with a zero point as the minimum of a black level or as the maximum of a white level. Moreover, each image data may be mapped with another value as the minimum of a black level or as the maximum of a white level.

The invention claimed is:

1. A radiographic apparatus comprising an image correcting unit for correcting offset of a detection value for every pixel to output corrected image data, the detection values being outputted from a radiation detector having pixels for detecting radiation arranged in a two-dimensional array,
wherein the image correcting unit comprises:
an offset-pammeter calculation unit calculating offset parameter as a time average of the detection values for every pixel upon taking dark images;

a fluctuation-noise calculation unit calculating a fluctuation noise that is a standard deviation of the detection values for every pixel upon taking dark images;

a correction constant calculation unit calculating a correction constant from the fluctuation noise for holding a negative value of a noise amplitude;

an offset correcting unit calculating an offset correction value by subtracting the offset parameter from the detection value at which a subject is imaged and adding the correction constant; and a gain correcting unit calculating corrected image data through multiplying a value, obtained by subtracting the correction constant from the offset correction value, by a gain correcting coefficient for correcting differences of the pixels in detecting property and then adding the correction constant, and wherein the image correcting unit corrects the offset while holding noise components contained in the detection value.

2. The radiographic apparatus according to claim 1, wherein the correction constant calculation unit calculates a correction constant based on a value of three times or more the fluctuation noise in the pixel.

3. The radiographic apparatus according to claim 2, wherein the correction constant calculation unit calculates the correction constant based on $3\sigma$ that is three times the fluctuation noise in the every pixel.

4. The radiographic apparatus according to claim 3, wherein the correction constant calculation unit calculates as the correction constant the maximum of $3\sigma$ in the every pixel.

5. The radiographic apparatus according to claim 1, further comprising:

a display unit displaying a fluoroscopic image of the subject; and an image constructing unit constructing the fluoroscopic image such that the corrected image data is set to correspond to a dynamic range of the display unit with the value of the correction constant as the minimum of a black level or the maximum of a white level.

6. A radiographic apparatus comprising an image correcting unit correcting offset of a detection value for every pixel to output corrected image data, the detection values being outputted from a radiation detector having pixels for detecting radiation arranged in a two-dimensional array, wherein the image correcting unit comprises:

an offset-parameter calculation unit calculating an offset parameter as a time average of the detection values for every pixel upon taking dark images;

an offset correcting unit calculating an offset correction value by subtracting the offset parameter from the detection value at which the subject is imaged; and a gain correcting unit calculating corrected image data through multiplying the offset correction value by a gain correcting coefficient for correcting differences of the pixels in detecting property, the offset correcting unit and the gain correcting unit performing calculation with plus and minus signs, the corrected image data to which gain correction has been performed in the gain correcting unit being image data with plus and minus signs; and wherein the image correcting unit corrects the offset while holding noise components contained in the detection value.

* * * * *